United States Patent [19]

Lisnyansky et al.

[11] Patent Number: 5,047,652
[45] Date of Patent: Sep. 10, 1991

[54] SYSTEM FOR ON-LINE MEASUREMENT OF COLOR, OPACITY AND REFLECTANCE OF A TRANSLUCENT MOVING WEB

[75] Inventors: Khaim Lisnyansky, Chester; Martin A. Hubbe, New Windsor, both of N.Y.

[73] Assignee: International Paper Company, Tuxedo Park, N.Y.

[21] Appl. No.: 509,589

[22] Filed: Apr. 16, 1990

[51] Int. Cl.⁵ .................... G01N 21/86; G01N 21/89
[52] U.S. Cl. .................................... 250/571; 356/429
[58] Field of Search ............... 356/73, 429, 430, 431, 356/434, 243, 249, 231, 424, 421; 250/571

[56] References Cited

U.S. PATENT DOCUMENTS

| | | |
|---|---|---|
| 2,246,501 | 6/1941 | Bradner et al. |
| 3,455,637 | 7/1969 | Howard |
| 3,476,482 | 10/1969 | Howard et al. |
| 3,936,189 | 2/1976 | De Remigis |
| 3,992,100 | 11/1976 | Lodzinski et al. |
| 4,015,904 | 4/1977 | De Remigis |
| 4,019,819 | 4/1977 | Lodzinski |
| 4,319,847 | 3/1982 | Howarth |
| 4,671,663 | 6/1987 | Sick |
| 4,690,564 | 9/1987 | Morgenstern et al. ............. 356/429 |
| 4,699,510 | 10/1987 | Alguard |
| 4,715,715 | 12/1987 | Howarth et al. |

Primary Examiner—David C. Nelms
Assistant Examiner—La Charles Keesee
Attorney, Agent, or Firm—Luedeka, Hodges, Neely & Graham

[57] ABSTRACT

Systems for the on-line optical measurement of properties of a translucent moving web, such as paper or plastic, as it is continually produced, colored or otherwise converted. Measured properties include color, reflectance and opacity. A backing roll has a cylindrical or approximately cylindrical surface which comprises at least one optical standard. The roll is positioned such that a circumferential portion of the roll surface contacts the back web surface where the web characteristic is to be measured, with the web curving around the circumferential portion. An optical sensing device is positioned so as to view the front web surface backed by the optical standard or standards. In several embodiments, two sets of reflectance data are collected, one with a "white" optical standard backing and the other with a "black" optical standard backing. The backing roll surface and the optical sensing device can be arranged such that the sensing device either alternately or simultaneously views portions of the front web surface backed by each of the optical standards. In other embodiments, the backing roll has a uniform optical standard surface.

24 Claims, 5 Drawing Sheets

SYSTEM FOR ON-LINE MEASUREMENT OF COLOR, OPACITY AND REFLECTANCE OF A TRANSLUCENT MOVING WEB

BACKGROUND OF THE INVENTION

The present invention relates generally to the on-line measurement of properties of a translucent moving web for process control and, more particularly, to the on-line measurement of color, reflectance and opacity of a moving web of paper as it is produced on a paper machine.

During the manufacture of paper, it is desirable to monitor characteristics such as color and opacity of paper as it is produced and to either continuously or periodically adjust process parameters to maintain desired characteristics of the paper being produced. Measurements of color and opacity are highly interrelated. Thus, measurements of color or reflectivity are sensitive to changes in opacity.

It is known to address the problem of color or reflectivity measurements being dependent upon opacity by backing the paper web with alternate black and white tiles and using the Kubelka-Munk formulas to estimate the reflectance of an infinitely thick stack of paper. Alternately, the paper web may be backed with a tile which matches the target reflectivity. As examples, De Remigis U.S. Pat. Nos. 3,936,189 and 4,015,904 disclose a stationary optical shoe assembly with white and black standards over which a web moves for measurement of color, opacity and brightness. A similar system is disclosed in Lodzinski et al U.S. Pat. No. 3,992,100 and Lodzinski U.S. Pat. No. 4,019,819.

The practice of using stationary or traversing flat black and white backgrounds behind the sheet material is well known to increase the likelihood of breakage of a sheet material such as paper as it is made on a paper machine. Contact between the paper and a flat stationary object also has the potential for producing scratch marks on the sheet material. Moreover, it is difficult to achieve complete contact between a moving web of paper and a stationary tile.

Accordingly, it is also known to employ backing tiles which are separated from the sheet material by an air gap. As examples, Howarth U.S. Pat. No. 4,319,847 discloses a system wherein a stream of air is employed to maintain a relatively constant spacing between a moving web, a standardization member below the web and a sensing head above the web. Similar systems with spacing are disclosed in Howard U.S. Pat. No. 3,455,637; and in Howarth et al U.S. Pat. No. 4,715,715. Although such practices can avoid adverse effects on productivity and sheet quality, several other problems are introduced. For example, the presence of an air gap changes the appearance of the translucent sheet material when viewed by the sensor over the backing. Formulas such as the Kubelka-Munk formulas for predicting the appearance of a thick sample are no longer valid. Such practices using a backing or backings not in contact with the sheet material are also subject to the possibility of fluctuations in the position of the material relative to the backing. The position is changed by variations in the thickness of the air gap.

An alternative approach uses a thick stack of the same sheet material as a backing behind the moving web of sheet material. This approach can suffer from a number of adverse effects, including: (a) fading of the material due to long exposure to light and environmental conditions in general; (b) wear, abrasion and mechanical damage of the backing if it is in direct contact with the moving web of sheet material; (c) error in reflectance measurement if the backing material is protected by a window; (d) an excessive amount of time and effort required to prepare different backings for each color of translucent product to be produced; (e) potential web damage due to contact of the moving web with a stationary stack of backing paper; (f) influence of the gap variation on the sheet reflectivity measurement; and (g) complexity of changing the backing with changes in product grade.

To solve the problems of fading, wear or both of the backing material, backing of a different material, such as ceramic, may be employed. However, such an approach is well known to require a greater amount of effort in preparing the backings and in matching the color of the sheet material to be measured or produced.

If no backing at all is employed behind the area of view on the sheet material, the measured reflectance of the material becomes a function of its opacity. This dependence of reflectance measurements on opacity is a source of major error of the color measurement, since the opacity varies for a number of reasons. For example, for paper there may be a change in thickness or basis weight of the sheet, filler content, hardwood-to-softwood ratio, sizing, and the like.

In this context, another approach is to separately measure reflectance of light from and transmission of light through the translucent sheet material. However, this approach differs fundamentally from the technique specified in the definition of opacity (TAPPI method T425 discussed hereinbelow), and correlation between the two methods is never perfect.

SUMMARY OF THE INVENTION

Accordingly, it is an object of the invention to provide an on-line system which compensates for variations in sheet opacity to accurately measure color or reflectance of translucent sheet material.

It is another object of the invention to provide such a system which measures sheet opacity with improved accuracy.

It is yet another object of the invention to provide a system which combines color and opacity measurements in one on-line system for improved reliability and reduced maintenance.

It is yet another object of the invention to achieve the foregoing while avoiding the disadvantages of stationary color tile optical standards and air gaps.

Briefly stated, and in accordance with an overall aspect of the invention, at least one characteristic of a moving web having front and back surfaces is optically measured by providing a backing roll having a surface which comprises at least one optical standard. The roll is positioned such that a circumferential portion of the surface contacts the back web surface where the web characteristic is to be measured, with the web curving around the circumferential portion. The roll rotates with a circumferential velocity that substantially equals the web velocity.

Positioned adjacent the circumferential portion of the roll surface so as to view the front web surface backed by the optical standard or standards is an optical sensing device which functions to measure one or more web characteristics. Preferably, the optical sensing device comprises an abridged spectrophotometer including an array of detectors for simultaneously measuring reflectance at a plurality of wavelengths. Preferably, two sets of reflectance data are collected, one with a background of high reflectance behind the sheet material, such as with a "white" backing, and the other with a backing of low reflectance behind the sheet material, such as with a "black" backing. (It will be appreciated that the terms "white" and "black" are relative rather than absolute terms.) However, the invention is also applicable to systems where all areas of the backing roll surface have the same uniform reflectance values, but with a limited system capability.

Depending upon the particular embodiment, the optical standards and the optical measuring device may be arranged such that the optical sensing device either alternately or simultaneously views portions of the front web surface backed by each of the optical standards.

In several embodiments the shape of the roll may be described as approximately cylindrical. However, it is usual in the art of papermaking to employ rolls having a slightly convex surface to compensate for bending of the roll due to web tension. In addition, one might consider alternative shapes, such as spheroidal, football-shaped, or slightly concave rolls. Rolls with rounded ends may be useful in embodiments where the rolls have a length less than the width of the web. Such short rolls may be an advantage when installed in a frame which contains sensors which view the top and the bottom of the web, respectively, at the same position relative to the direction of manufacture.

In accordance with one specific embodiment of the invention wherein the optical sensing device alternately views portions of the front web surface backed by each of the optical standards, the surface of the backing roll is generally axially divided into two portions respectively comprising the two different optical standards. The portions meet at an intermediate position on the surface at a boundary defined by the intersection of a plane with the surface, the plane intersecting the axis at an angle other than 90°, preferably intersecting at a 45° angle or lower. The optical sensing device is positioned along the roll generally at the intermediate position such that, as the backing roll rotates, the sensing device alternately views portions of the front web surface backed by each of the optical standards.

In various alternative embodiments, rather than providing two different optical standards which meet at a boundary angled at 45°, at least a portion of the roll surface along the axis of the roll is circumferentially divided, that is, with boundaries parallel to the roll axis, into at least two portions respectively comprising the two different optical standards. The optical sensing device again is positioned along the roll generally over the circumferentially divided portions such that the sensing device alternately views portions of the front web surface backed by each of the optical standards as the backing roll rotates. In a case where the circumferentially divided axial portion of the backing roll extends along substantially the entire width of the roll, the optical sensing device may be provided with a scanning mounting operable to traverse in a direction parallel to the roll axis such that measurements can be made across the width of the web. In a variation, the circumferentially divided portion is circumferentially divided into a plurality of alternating optical standard segments alternately corresponding to the two different optical standards.

In those embodiments where the sensing device alternately views portions of the front web surface backed by each of the optical standards as the backing roll rotates, an angular position encoder may be connected to the backing roll for synchronizing system timing to the angular position of the backing roll. As a result, the particular optical standard backing the viewed portion of the front web surface at a given instant in time can be determined for proper recording of measurements.

In other embodiments of the invention, the surface of the backing roll is generally axially divided into two portions respectively comprising the two different optical standards and the optical sensing device is arranged to either alternately or simultaneously view portions of the front web surface backed by each of the optical standards independently of roll rotation.

In one embodiment, the optical sensing device includes a movable mounting operable to alternately position the optical sensing device over the optical standard portions. Alternatively, the optical sensing device may be provided with two sets of elements respectively positioned for simultaneously viewing portions of the front web surface backed by the two different optical standards. As another alternative embodiment, the optical sensing device includes a shifting mirror to alternately view portions of the front web surface backed by the two optical standard portions.

In a related embodiment, the surface of the backing roll is axially divided into a plurality of alternating optical segments alternately corresponding to the two different optical standards, and the optical sensing device includes a scanning mounting operable to traverse in a direction parallel to the roll axis such that the optical sensing device alternately views portions of the front web surface backed by segments corresponding to the two different optical standards.

In another embodiment at least one part of the backing roll has a reflectance spectrum which is substantially equal to the desired reflectivity spectrum of the web material. Likewise, other portions of the backing roll surface may have different reflectance spectra which match the desired specifications for additional colors or shades of the web material.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

DETAILED DESCRIPTION OF THE PREFERRED EMBODIMENTS

Figure 1:
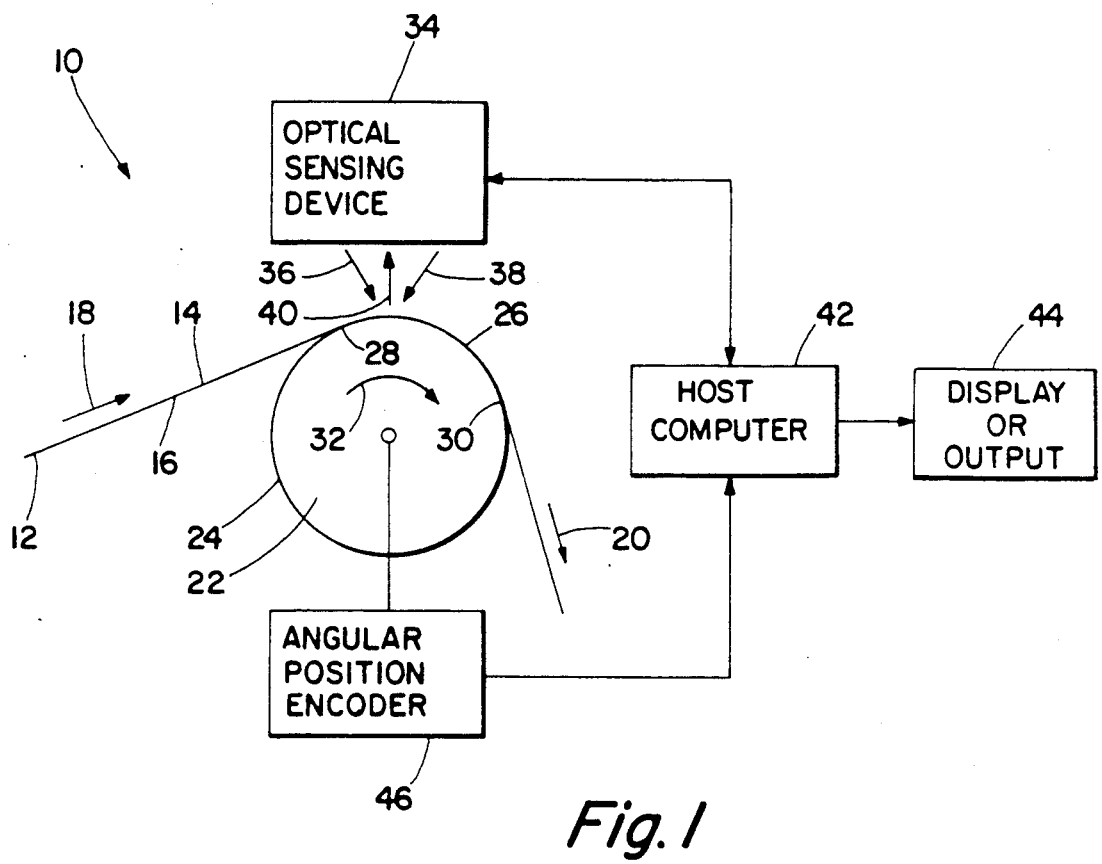
FIG. 1 is an overall block diagram of a system in accordance with the invention.

Referring now to the drawings in which like reference numerals designate like or corresponding elements throughout the several views, FIG. 1 depicts in block diagram form an on-line system generally designated 10 in accordance with the invention for optically measuring at least one characteristic of a moving web 12. Web characteristics which may be measured include color, opacity and reflectance. The web 12 typically comprises paper, and as such is translucent, rather than completely opaque. The web 12 has front 14 and back 16 surfaces, and moves in a direction indicated by arrows 18 and 20.

A backing roll 22 is provided having a surface 24 which comprises at least one optical standard. The roll 22 is positioned such that a circumferential portion 26 of the roll surface 24 beginning approximately at a point 28 and ending approximately at a point 30 contacts the back web surface 16 where the web characteristic is to be optically measured. Thus, the web 12 curves around the circumferential portion 26. The roll 22 rotates clockwise as indicated by an arrow 32 with a circumferential velocity that substantially equals web velocity such that there is no relative motion between the web 12 and the circumferential portion 24 as the web 12 passes over the roll 22.

For measuring web characteristics, an optical sensing device 34 is positioned adjacent the circumferential portion 26 of the roll surface 24 so as to view the front web surface 14 backed by the one or more optical standards of the surface 24. Incident illumination from the optical sensing device 34 is represented by arrows 36 and 38, while light diffusely reflected away from the front web surface 14 is represented by arrow 40.

While the optical sensing device 34 is described in detail with reference to FIG. 2, at this point it may be noted that the optical sensing device 34 is interconnected with a host computer 42 for determining the properties being measured. The host computer 42 in turn is illustratively connected to a display or output device 44, which may comprise a printer, a video display, or suitable feedback connections to control process parameters, as will be appreciated by those skilled in the art.

The remaining element depicted in FIG. 1 is an angular position encoder 46, likewise connected to the host computer 42, and employed in the particular embodiments where the particular optical standard backing the portion of the web 12 viewed by the optical sensing device 34 depends upon angular position of the roll 22. Such embodiments are described hereinbelow with reference to FIGS. 3, 4, 5A and 5B. In other embodiments, described hereinbelow with reference to FIGS. 6, 7, 8 and 9, the particular optical standard backing the portion of the web 12 viewed by the optical sensing device 34 does not depend upon angular position of the roll 22, but rather upon position or other characteristic of the optical sensing device 34.

Before continuing with a detailed description of apparatus embodying the invention, principles relating to optically measuring characteristics such as color, opacity and reflectance of translucent sheet material are briefly summarized next.

The fraction of incident monochromatic light which is diffusely reflected back from a sample is known as the diffuse reflectance of the sample at the wavelength of the incident light. Reflectivity is the reflectance of a sufficiently thick stack of identical sample. The stack is sufficiently thick if a further increase in thickness has no effect on the output. In the case of a sample having a very high opacity, measured reflectance may equal reflectivity. Reflectivity is a fundamental property of a material and forms the basis for matching the color of translucent sheets of materials such as paper. Reflectivity data are used in order to calculate appearance properties such as International Commission on Illumination (CIE) tristimulus values, chromaticity coordinates, and color-difference quantities such as Hunter-Lab and CIE-L*a*b* under a variety of different assumed conditions of illumination.

In samples which are not completely opaque, the measured reflectance may be a function of the presence and reflective properties of a background. Color values calculated on the basis of such reflectance values will be in error. In addition, the error due to the background may vary in an uncontrolled way if there are uncontrolled variations in the basis weight or the opacifying efficiency of the translucent sheet material. However, by using a backing roll in accordance with the invention, accurate information about the reflectivity of translucent sheet materials can be obtained. As described above, the backing roll surface is in complete contact with and moves at the same velocity as the web of translucent sheet material.

Preferably, and as described in detail hereinafter, the roll surface 24 is divided into "black" and "white" sections comprising optical standards. The terms "black" and "white" are used in a qualitative, rather than a quantitative sense here, since it is not necessary that either surface approach the ideal cases of 100% reflectance or 0% reflectance over the spectral range of interest. There must, however, be a large difference in reflectance between the two at all wavelengths of interest.

In the preferred system, two sets of reflectance data are collected, one with a background of high reflectance behind the sheet material (henceforth referred to as $R_{white}$) and one with a background of low reflectance behind the sheet material ($R_{black}$). The reflectance of the highly reflective background by itself is referred to herein as $R_{g\text{-}white}$.

Assuming first that the "black" background has a reflectance $R_{g\text{-}black}$ close to 0% at the wavelength of interest, values of $R_{white}$, $R_{black}$, and $R_{g\text{-}white}$ are measured and stored in a system memory. An equation to estimate the reflectivity of an infinite thickness of the same sheet material is given by "Reflectance Spectroscopy" by Wendlandt and Hecht, Wiley and Sons 1966 as follows:

$$Reflectivity = R_\infty = a - (a^2 - 1)^{0.5}$$

where $$a = 0.5 \cdot \left[ R_{white} + \frac{R_{black} - R_{white} + R_{g\text{-}white}}{R_{black} \cdot R_{g\text{-}white}} \right]$$

Alternatively, if the "black" background cannot be treated as if it has a true zero reflectance at the wavelength of interest, it may be necessary to consider the reflectance of each of the backgrounds. The Kubelka-Munk estimate of the reflectance of an infinite stack will be a solution to the expression $$\frac{(1 - R_{white} \cdot R_\infty)(R_\infty - R_{g\text{-}white})}{(1 - R_{g\text{-}white} \cdot R_\infty)(R_\infty - R_{white})} =$$

$$\frac{(1 - R_{black} \cdot R_\infty)(R_\infty - R_{g\text{-}black})}{(1 - R_{g\text{-}black} \cdot R_\infty)(R_\infty - R_{black})}$$

An alternative equation to be used in place of the Kubelka-Munk equation, but for the same purpose, was given by W. L. Bracken in "In-Mill Evaluation of Optical Efficiency of Coatings," TAPPI 64 (5): 59-62 (May 1981) as follows:

$$R_\infty = \frac{(R_{white} \cdot R_{g\text{-}black} - R_{black} \cdot R_{g\text{-}white})}{(R_{white} - R_{black} - R_{g\text{-}white} + R_{g\text{-}black})}$$

In addition, it is also feasible to use a regression of data in order to determine functions of the variables $R_{white}$, $R_{black}$ and the corresponding reflectances of the two backgrounds in order to estimate the value of an infinitely thick stack of the translucent sheet material being measured.

The same data can be used to determine the opacity of the translucent sheet material. In the Technical Association of the Pulp and Paper Industry (TAPPI) procedure T425, the "white" background is defined as having a reflectance of 89%, using a well-defined illuminant centered about the wavelength 572 nm. The "black" background is defined as having zero reflectance over the same spectral region. The percent opacity determined by this technique is given by 100 times $R_{black}/R_{white}$.

When using the system of the invention for on-line measurements of opacity, it may not always be feasible or desirable for the areas of the roll designated as "white" to match the reflectance criteria defined in the TAPPI procedure T425. In such cases, the TAPPI opacity $C_{0.89}$ can be calculated from the reflectivity R and the measured reflectance values $R_\infty$ over a background having reflectance $R_g$ at each wavelength as follows:

$$C_{0.89} = \frac{(-1 + a)[0.89 - R_\infty - (0.89 - 1/R_\infty)a]}{(-R_\infty + a/R_\infty)[0.89/R_\infty - 1 - R_\infty(0.89 - 1/R_\infty)a]}$$

where
$a = \exp[sW (1/R_\infty - R_\infty)]$ $$sW = \frac{1}{1/R_\infty - R_\infty} \ln\left[ \frac{R R_g R_\infty - R R_\infty^2 - R_g + R_\infty}{R R_g R_\infty - R - R_g R_\infty^2 + R_\infty} \right]$$

The quantity s is the Kubelka-Munk scattering coefficient, and W is the weight per unit area of sheet metal.

Alternatively, the data may be used to calculate a quantity generally known as printing opacity, defined in TAPPI method T519. Printing opacity C is given by $R_o/R_\infty$, where $R_o$ is defined as $R_{black}$ in the case of a background having zero reflectance. The quantity $R_o$ may be calculated from $$C_\infty = R_o/R_\infty = \frac{-1 + a}{-R_\infty^2 + a}$$

Figure 2:
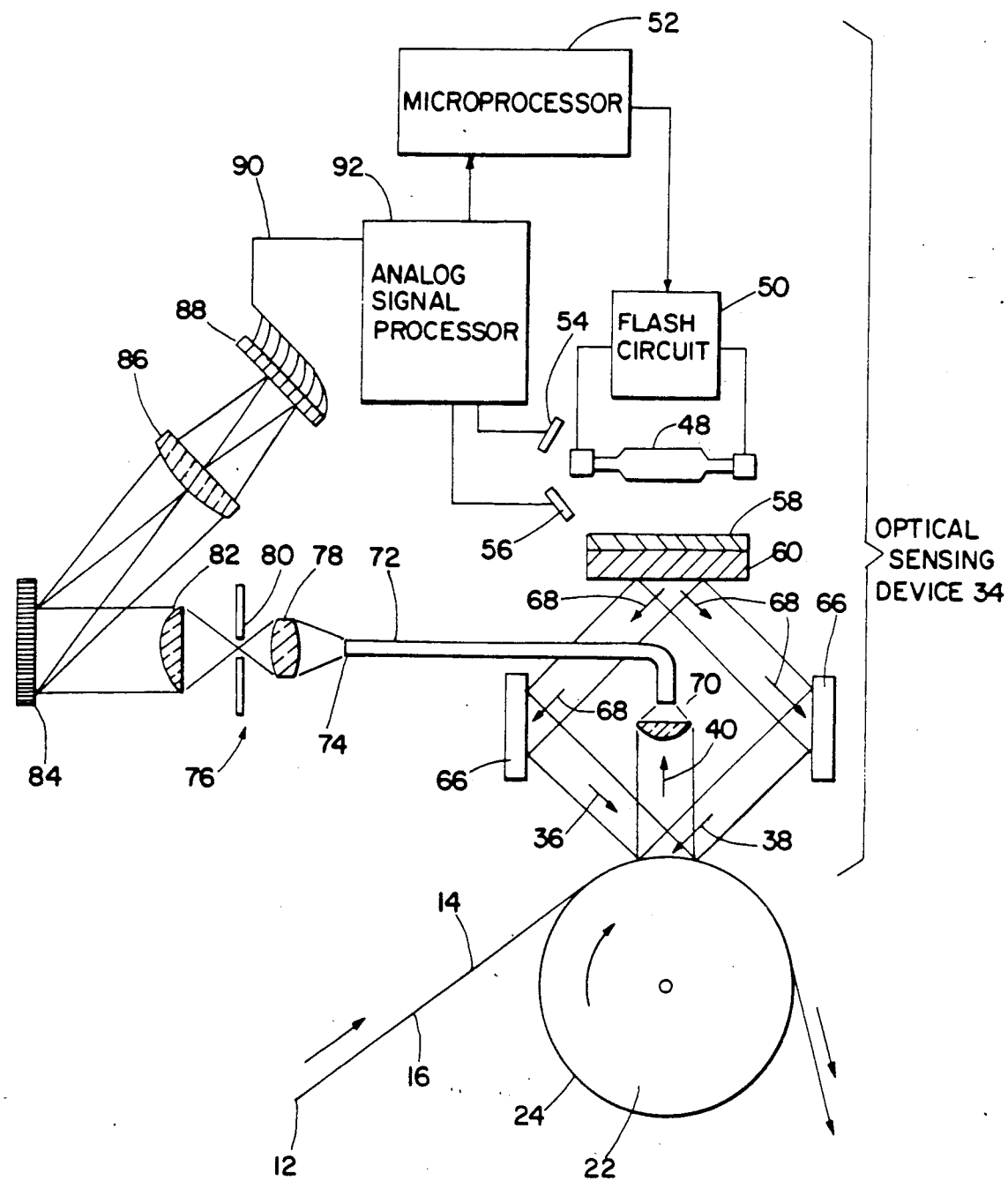
FIG. 2 depicts in greater detail the optical sensing device of FIG. 1.

Referring now to FIG. 2, illustrated is a suitable construction of the optical sensing device 34 of FIG. 1. For purposes of relating the various elements to one another, FIG. 2 also depicts the web 12, the roll 22, incident illumination arrows 36 and 38, and reflected light arrow 40.

In general, the optical sensing device 34 may be viewed as an abridged spectrophotometer, an instrument which measures the fraction of incident light which is diffusely reflected from a sample as a function of the wavelength of light. An abridged spectrophotometer differs from the usual scanning spectrophotometer in that it employs an array of detectors which simultaneously sense different wavelengths for increased measurement speed, and as such is advantageous for on-line measurements of color.

The optical sensing device 34 includes a xenon flash lamp 48 driven by a suitable flash circuit 50 under control of a microprocessor 52. For calibration and reference purposes, a pair of photodiodes 54 and 56 are positioned so as to sense the level of illumination from the xenon flash lamp 48.

In order to match the spectral characteristics of the light thus produced to a standard light source, a suitable optical filter 58 is provided. A diffuser 60 follows the filter 58. To illuminate the front surface 14 of the web backed by the optical standard or standards on the roll 22 surface 24 at approximately a 45° angle, an annular ring mirror 66 directs light from the diffuser 60 represented by arrows 68 to produce the incident illumination represented by the arrows 36 and 38.

A collecting lens 70 connected to a fiberoptic bundle 72 is provided to collect light which is diffusely reflected away from the front surface 14 of the web 12 as indicated by arrow 40. At the end 74 of the fiberoptic bundle 72 is a refocusing assembly 76 including a lens 78, an entrance slit 80 and a collimating lens 82. Collimated light from the lens 82 strikes a diffraction grading 84 to produce a color spectrum, which is then focused by an integrating lens 86 on to an array 88 of individual photodiodes having outputs connected along a bus 90 to an analog signal processor 92.

The analog signal processor 92 comprises conventional comparator and analog-to-digital conversion circuitry to compare normalized magnitudes from the photodiodes of the array 88 with signals from the reference photodiodes 54 and 56 to provide digitized spectral signals to the microprocessor 52. Measurements are synchronized with the roll position by means of the angular position encoder 46 (FIG. 1) in those embodiments where the particular optical standard backing the viewed portion of the web 12 depends upon angular position of the roll 22. Although processing is shown distributed between the FIG. 1 host computer 42 and the FIG. 2 microprocessor 52, it will be appreciated that the calculations and control functions performed by each are a matter of design choice, and a variety of architectures may be employed.

Thus, it will be appreciated that the sensor 34, in combination with the optical standards backing the web 12, provide sufficient data from which to determine the characteristics of the web to be measured, in view of the general principles relating to optically measuring characteristics such as color, reflectance and opacity of translucent sheet material as summarized hereinabove.

As an alternative, instead of using an abridged spectrophotometer, it will be appreciated that a continuous scanning spectrophotometer can be employed. However, the abridged spectrophotometer sensor is preferred for continuous on-line measurements because of its inherently greater speed.

As another alternative to an abridged spectrophotometer, a filter colorimeter may be employed. Instead of measuring reflectance properties at many different wavelengths of light, a typical colorimeter measures just three reflectance values corresponding to the spectrosensitivity of three types of receptors in the human eye. However, each of the three reflectance outputs can be treated by the same procedures and mathematics described for the preferred system. Well known equations are available to calculate various quantities describing color based on the output of a colorimeter used in this manner. However, a spectrophotometer may be preferred because it is not feasible to use the output of a filter colorimeter to predict how a sample will look under conditions of illumination which differ from those used by the instrument. Thus, the colorimeter cannot detect metameric differences between samples.

As yet another alternative to an abridged spectrophotometer, a device which senses the fraction of incident light which is diffusely reflected at one wavelength or over a defined distribution of light intensity can be employed. For instance, the device may have the same spectrosensitivity as is defined in TAPPI method T452 for brightness determination. The procedures and calculations described for the preferred system can be used to determine the brightness of the translucent sheet material while making the result independent of opacity. If the spectrosensitivity of the device matches that of TAPPI method T425 (opacity), the system can be used to measure TAPPI opacity.

Figure 3:
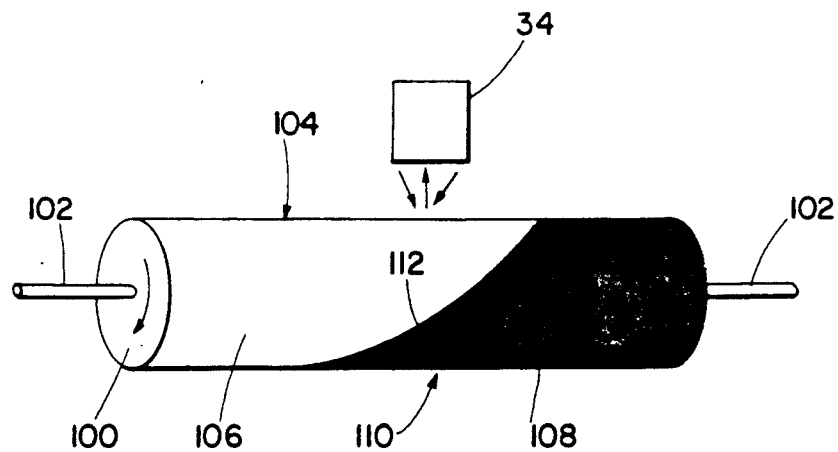
FIG. 3 depicts an embodiment of an optical standard roll surface, and the relationship of the optical sensing device.

FIG. 3 depicts a presently preferred form of backing roll surface comprising a pair of optical standards. In FIG. 3, a backing roll 100 (the moving web is not shown) has an axis of rotation represented by a shaft 102 and a surface 104 generally axially divided into two portions 106 and 108 respectively comprising the "white" and "black" optical standards. The portions 106 and 108 meet at an intermediate position generally designated 110 on the roll surface 104 at a boundary 112 defined by the intersection of a plane with the roll surface 104, the plane intersecting the axis represented by the shaft 102 at an angle other than 90°, preferably at an angle of 45° or lower. The optical sensing device 34 is positioned along the roll 100 generally at the intermediate position 110 such that the sensing device 34 alternately views portions of the front web surface 14 (FIGS. 1 and 2) backed by each of the optical standards 106 and 108 as the backing roll 100 rotates. System timing and the recording of measurements are synchronized with the angular position of the roll 100 by means of the FIG. 1 angular position encoder 46.

It will be appreciated that the precise angle of the boundary 112 of the "white" 106 and "black" 108 optical standards is not critical, so long as rotation of the roll 100 causes alternate "white" and "black" optical standards to be positioned as a backing below the area of sheet material viewed by the sensor 34.

One way in which the roll 100 of FIG. 3 may be constructed is to first prepare black and white hollow cylinders, each having the same inside and outside diameters. One end of each cylinder is cut at the same fixed angle relative to its axis. A support roll (not shown) having the same outer diameter as the inner diameter of the two cylinders is inserted into both such that the two cylinders fit tightly together at the angular cut.

Figure 4:
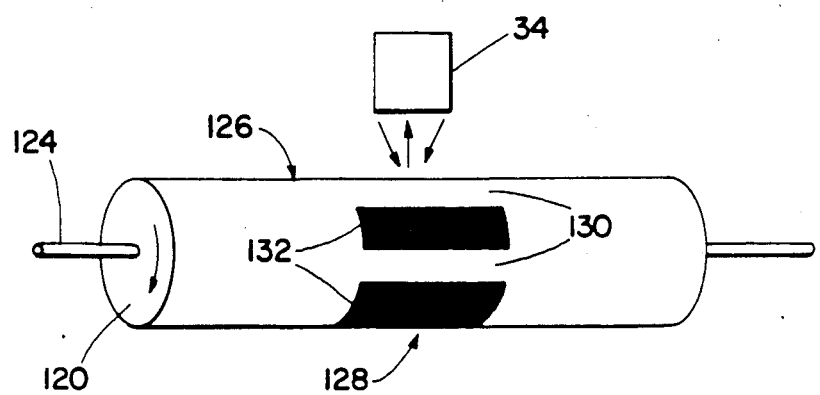
FIG. 4 depicts another embodiment of an optical standard roll surface, and the relationship of the optical sensing device.
Figure 5A:
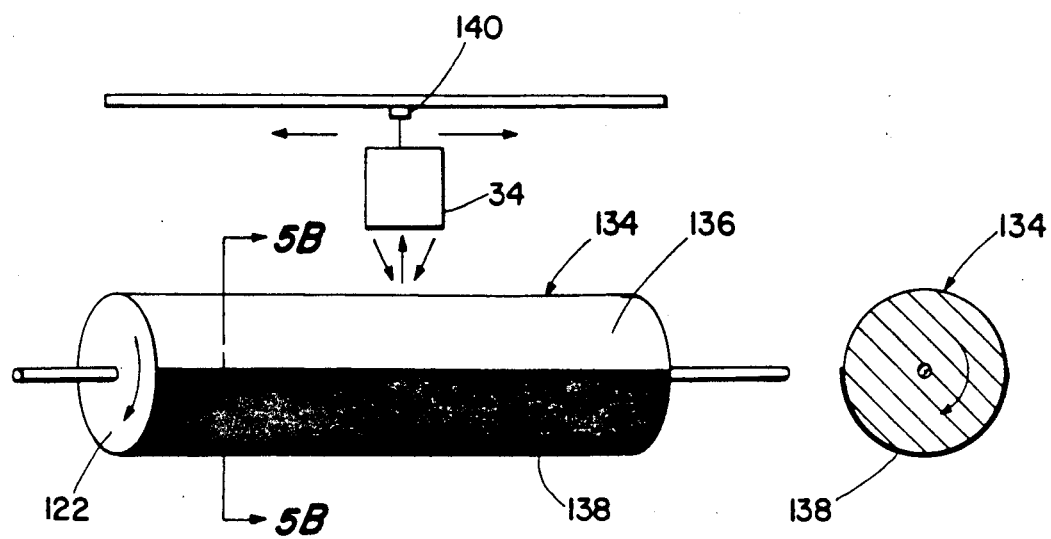
FIG. 5A, and FIG. 5B, which is a section taken along line 5B—5B of FIG. 5A, depict yet another embodiment of an optical standard roll surface, and the relationship of the optical sensing device.
Figure 5B:
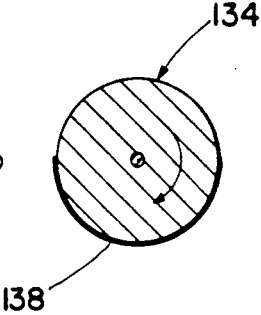

FIG. 4 and FIGS. 5A and 5B respectively illustrate two alternative optical standard rolls 120 and 122 (moving web 14 is not shown) wherein at least a portion of the roll surface along the roll axis is circumferentially divided into at least two portions respectively comprising the "white" and "black" optical standards. Thus, in each case boundaries between the "white" and "black" optical standard portions are parallel to the roll axis. Again, in each case timing and recording of measurements are synchronized with the angular position of the roll by means of the angular position encoder 46 (FIG. 1).

More particularly, in the embodiment of FIG. 4, the roll 120 has an axis of rotation represented by a shaft 124 and a surface 126 having a portion generally designated 128 circumferentially divided into a plurality of alternating optical standard segments alternately corresponding to the "white" 130 and "black" 132 optical standards. The optical sensing device 34 is positioned along the roll 120 generally over the circumferentially divided portion 128 such that the sensing device 34 alternately views portions of the front web surface 14 (FIGS. 1 and 2) backed by each of the "white" and "black" optical standards as the backing roll 120 rotates.

In the embodiment of FIGS. 5A and 5B, the roll 122 has a surface 134 and the circumferentially divided axial portion of the surface 134 is substantially the entire width of the roll 122. Thus, one semi-cylindrical or approximately semi-cylindrical half 136 of the roll surface 134 comprises the "white" optical standard, and the other semi-cylindrical or approximately semi-cylindrical half 138 of the roll surface 134 comprises the "black" optical standard.

The optical sensing device 34 includes a scanning mounting represented at 140 operable to traverse in a direction parallel to the roll axis such that measurements can be made across the width of the web 12.

Figure 6:
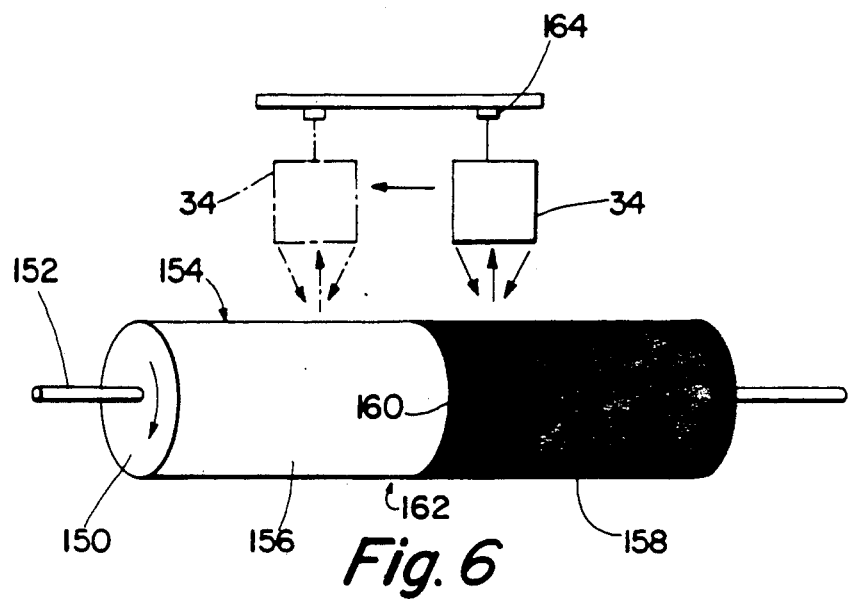
FIG. 6 depicts another embodiment of an optical standard roll surface, and one form of optical sensing device.
Figure 7:
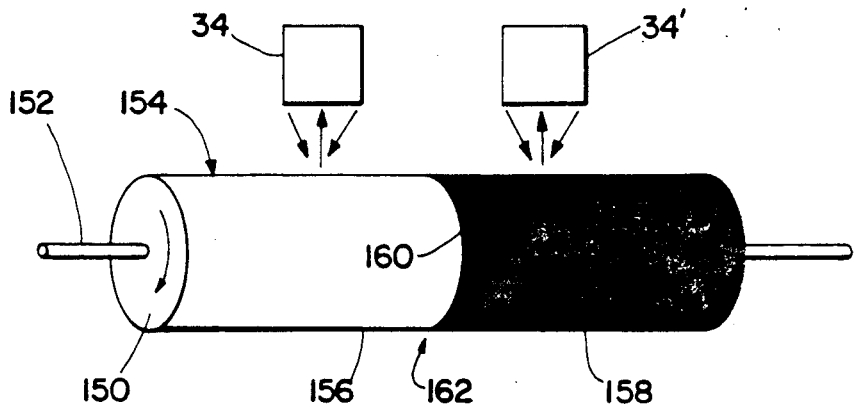
FIG. 7 depicts an optical standard roll surface like that of FIG. 6, with another form of optical sensing device.
Figure 8:
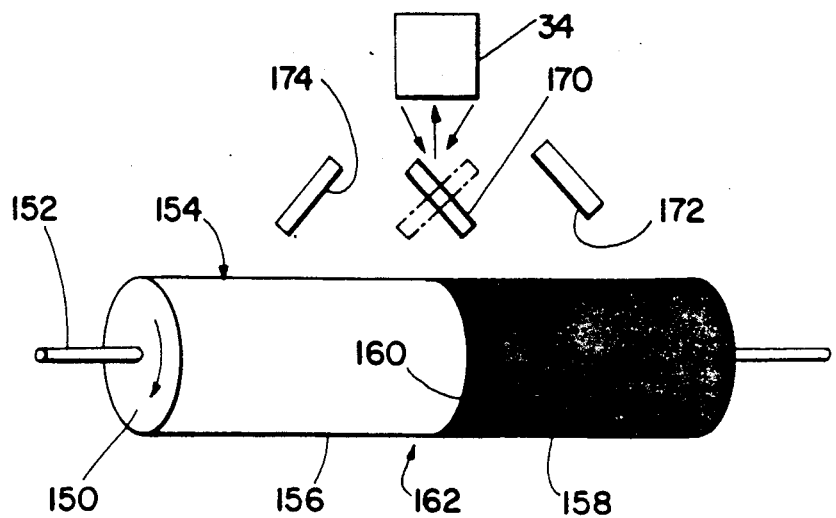
FIG. 8 depicts an optical standard roll surface like that of FIG. 6, with yet another form of optical sensing device.

FIGS. 6, 7 and 8 depict three alternative embodiments wherein the angular position of the roll does not affect which of the two optical standards is backing the web 12 for a particular measurement. Rather, it is the optical sensing device 34 which determines the particular optical standard backing in effect at a particular time.

In all three FIGS. 6, 7 and 8, a backing roll 150 (the moving web 14 is not shown) has an axis of rotation represented by a shaft 152 and a surface 154 generally axially divided into "white" 156 and "black" 158 optical standard portions. The "white" 156 and "black" 158 optical standard portions meet at a boundary 160 on an intermediate position generally designated 162 of the surface 154. Unlike the embodiment of FIG. 3, in FIGS. 6, 7 and 8 the boundary 160 is defined by the intersection of a plane with the surface 154 at an angle of 90° with reference to the roll axis, although it will be appreciated that a slight "wobble" in the position of the boundary 160 as the roll 150 rotates does not affect the measurements, provided the optical sensing device 34 is positioned sufficiently far away from the boundary 160 during measurement.

In the embodiment of FIG. 6, the optical sensing device 34 includes a movable mounting (scanning system) represented at 164 operable to alternately position the optical sensing device 34 over the "white" 156 and "black" 158 optical standard portions such that the sensing device 34 alternately views portions of the front web surface 14 (not shown) backed by each of the "white" and "black" optical standards as the sensing device 34 is alternately positioned. Shown in solid lines in FIG. 6 is the optical sensing device 34 positioned over the "black" optical standards, and its alternative position is shown in phantom.

In the embodiment of FIG. 7, the optical sensing device includes two sets of elements 34 and 34' respectively positioned for viewing portions of the front web surface 14 backed by the "white" 156 and "black" 158 optical standards simultaneously. It will be appreciated that the optical sensing devices 34 and 34' depicted in FIG. 7 correspond to the optical sensing device shown in FIG. 2, and that various numbers of the FIG. 2 elements may be common as between the two devices 34 and 34' of FIG. 7, as a matter of design choice. Thus, the design can range from essentially entirely duplicating the FIG. 2 arrangement in each of the optical sensing devices 34 and 34' of FIG. 7, to sharing various elements such as the microprocessor 52, the flash circuit 50 and flash lamp 48, and the analog signal processor 92, as a matter of design choice.

In the embodiment of FIG. 8, the optical sensing device 34 includes an optical path shifting device such as a shifting mirror 170 to alternately view portions of the front web surface 14 backed by the "white" 156 and "black" 158 optical standard portions. More particularly, the mirror 170 is silvered on both sides, and shifts between the position illustrated in solid lines and the position illustrated in phantom. Cooperating with the mirror 170 are a pair of fixed mirrors 172 and 174 positioned generally over the "white" 156 and "black" 158 optical standard portions. Equivalent optical path shifting devices may be employed, such as a moveable prism.

Figure 9:
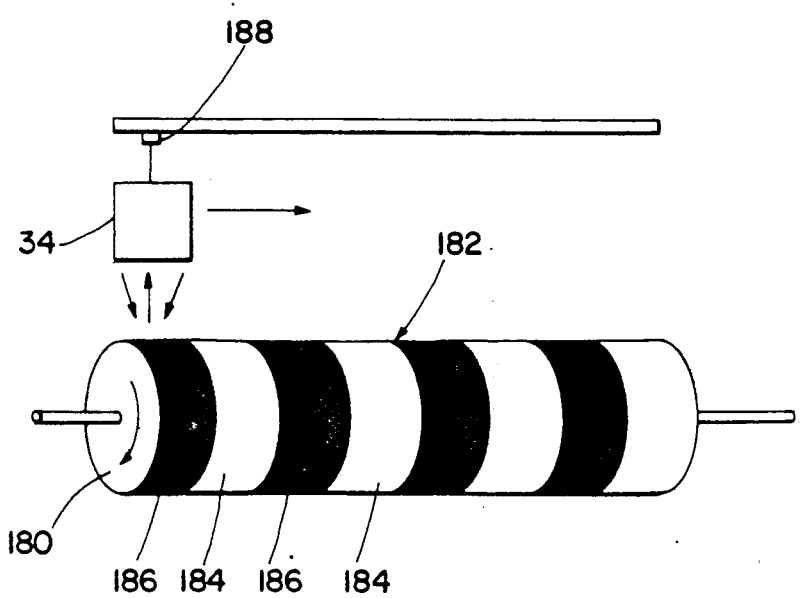
FIG. 9 depicts still another embodiment of an optical standard roll surface, and the relationship of the optical sensing device.

FIG. 9 depicts an alternative embodiment wherein a roll 180 has a surface 182 axially divided into a plurality of alternating optical standard segments 184 and 186 respectively corresponding to the "white" and "black" optical standards. In FIG. 9, the optical sensing device 34 includes a scanning mounting represented at 188 operable to traverse over the moving web 14 (not shown) in a direction parallel to the axis of the roll 180 such that the optical sensing device 34 alternately views portions of the front web surface 14 backed by segments corresponding to the "white" and "black" optical standards.

In each of the embodiments of FIGS. 3, 4, 5A, 5B, 6, 7, 8 and 9, two different and contrasting optical standards are employed. However, as generally represented in FIGS. 1 and 2, where no particular form of backing roll pattern is shown, the backing roll may have a uniform optical standard surface, or at least a portion of its surface which backs a portion of the web viewed by the sensor 34 may be uniform.

For example, the roll may be constructed of a color which matches the target color of the translucent sheet material. Thus, a white backing roll can be used in the case of white paper in order to reduce the error when measured reflectance values are used as an indication of sample reflectivity.

One way to produce a roll having the same color as the translucent sheet material is to wrap a sufficient number of thicknesses of the sheet material around a roll. Adhesive or fasteners may be used to hold the sheet material in place. The number of layers of sheet material at any location on the roll should be sufficient such that a further increase in the number of layers has a minor effect on reflectance properties.

Another way to produce such a backing roll is to use a material which is different from the translucent sheet material but has the same reflectance as the target.

In either case, the principle behind the use of a uniform backing roll is that if the reflectivity of the translucent sheet material matches the reflectance of the backing roll, then the measured reflectance is the same as would be measured from a thick stack of sample. Only a relatively small deviation of the measured reflectance from reflectivity will occur when the translucent sheet material differs to only a small degree from the backing.

It will be appreciated however that, when all areas of the backing roll surface have the same uniform reflectance value versus wavelength of light, it is not feasible to use the reflectance measurements as a means of determining opacity.

In a hybrid approach, the surface of the backing roll includes optical standard areas of at least two contrasting reflectances, and one of these areas matches the target of the translucent sheet material. For instance, if the sheet material is white in color, the reflectance of the sample over a matching white background may be used directly in determining the color of the sheet material. In order to determine the opacity of the same sheet material, values of reflectance are also measured over a black background. Subsequent calculations are the same as in the preferred system as described hereinabove.

As a variation on the system just described, the reflectance of two areas on the backing roll may be chosen so that one of them matches the reflectivity of a translucent sheet material which has a color other than white. This approach is feasible only if the frequency and duration of measurements of the given color are sufficient to justify installation of a roll with part of the surface matching the target reflectivity. Also, it is necessary that the two contrasting areas of the backing roll differ greatly in reflectance over the whole spectral range tested.

Figure 10:
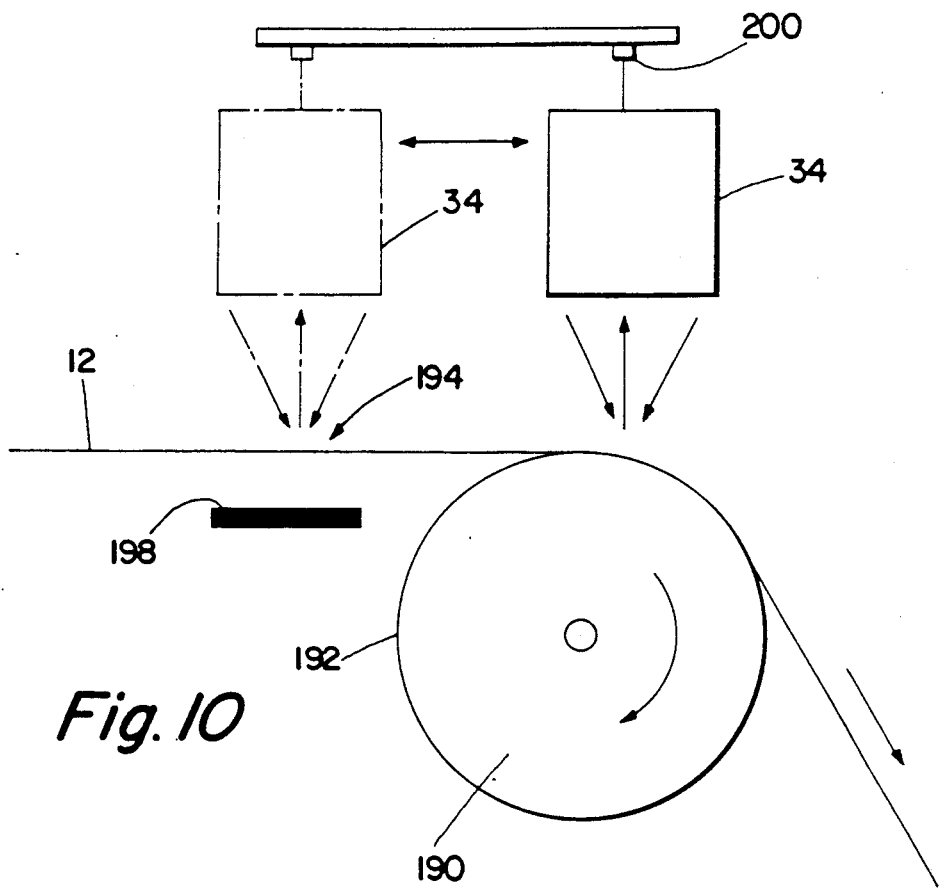
FIG. 10 depicts an embodiment wherein the optical sensing device alternately views portions of the web surface backed by an optical standard roll and by an air gap.

FIG. 10 depicts an embodiment which allows the measurement of opacity even where there is no black optical standard on the backing roll surface. In cases where the translucent sheet material has a color which differs from the optical standard, this embodiment facilitates corrections for the effect of variations in opacity on the measured reflectance.

More particularly, in FIG. 10 a backing roll 190 has a surface 192 which comprises either a white optical standard or an optical standard which matches the desired reflectivity of the web 12 of translucent sheet material. At a site 194 adjacent the roll 190 the web 12 is backed either by an air gap 196 or, preferably, by a black or dark-colored surface 198 separated by the air gap 196 and not in contact with the web 12 of sheet material. Backing by the black surface 198 separated by the air gap 196 and not in contact with the sheet material 12 is equivalent to backing the sheet material with a black standard.

The optical sensing device 34 in FIG. 10 includes a movable mounting (scanning system) represented at 200 operable to alternately position the optical sensing device 34 over the roll surface 192 and over the site 194, as depicted in phantom. Thus the optical sensing device 34 alternately measures the reflectance of the translucent sheet material 12 backed by the optical standard and by the air gap 196.

Figure 11:
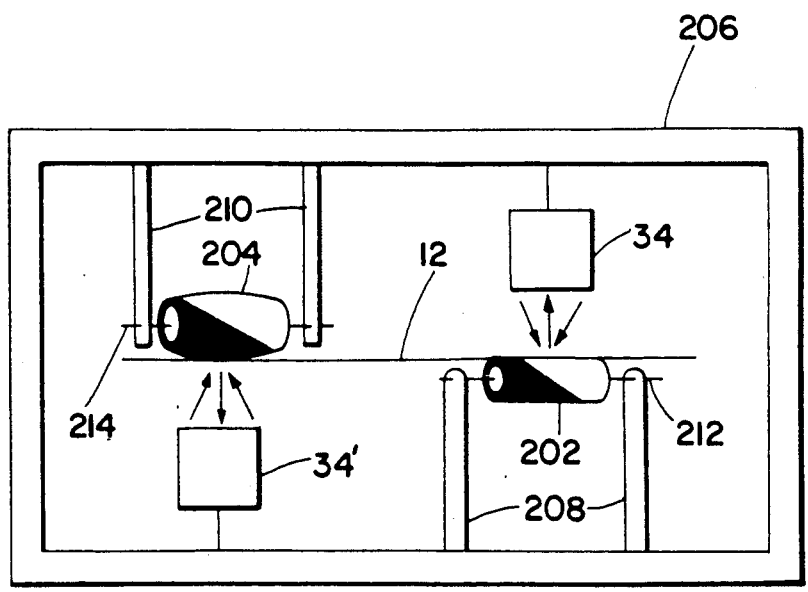
FIG. 11 depicts an embodiment wherein a pair of reduced-length optical standard backing rolls are employed.

Finally, FIG. 11 depicts an embodiment where sensors 34 and 34' view the top and bottom of the web 12 at the same position relative to the direction of travel, employing a pair of optical standard backing rolls 202 and 204 having lengths less than the width of the web 12. While it is generally preferred to employ a backing roll which extends across the entire width of the web of translucent sheet material, embodiments such as that of FIG. 11 may be employed in order to save space, although the use of backing rolls which do not extend the full width of the web are not preferred due to concerns about maintaining parallel tracking and runability of the web through a paper machine.

In FIG. 11, a single frame 206 is employed to support the sensors 34 and 34' respectively viewing the top and bottom of the web 12 respectively backed by the rolls 202 and 204, also supported by the frame 206 through supports 208 and 210, and rotating shafts 212 and 214. In order to prevent damage to the web 12, the rolls 202 and 204 may have rounded ends. Alternatively, a convex or spheroidal backing roll surface may be employed in order to contact the web material only at a limited area opposite the sensor 34 or 34'.

In view of the foregoing, it will be appreciated that the invention provides a system which permits measurements of the reflectivity or color of a translucent sheet material, which measurements would otherwise be sensitive to changes in the opacity of the sheet material. At the same time, the system of the invention does not damage the sheet material, nor result in a decrease in the rate of production.

The system of the invention also permits more accurate determinations of opacity without damage to the sheet material or decrease in the rate of production. Because opacity measurements are obtained by the same system, it is not necessary to purchase, maintain and calibrate two separate instruments to obtain both color and opacity measurements.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. An on-line system for optically measuring at least one characteristic of a web having front and back surfaces and moving with a velocity, said system comprising:

a backing roll having a surface which comprises at least one optical standard, said roll positioned such that a circumferential portion of said surface contacts the back web surface where said at least one characteristic is to be measured, the web curving around said circumferential portion, and said roll rotating with a circumferential velocity that substantially equals the web velocity; and an optical sensing device positioned adjacent said circumferential portion of said roll surface so as to view the front web surface backed by said at least one optical standard for measuring said at least one web characteristic.

2. An on-line system in accordance with claim 1, wherein said backing roll surface comprises two different optical standards.

3. An on-line system in accordance with claim 2, wherein said optical standards and said optical sensing device are arranged such that said optical sensing device alternately views portions of the front web surface backed by each of said optical standards.

4. An on-line system in accordance with claim 2, wherein said optical standards and said optical sensing device are arranged such that said optical sensing device simultaneously views portions of the front web surface backed by each of said optical standards.

5. An on-line system in accordance with claim 3, wherein:

said backing roll has an axis of rotation and said surface is generally axially divided into two portions respectively comprising said two different optical standards, said portions meeting at an intermediate position on said surface at a boundary defined by the intersection of a plane with said surface, said plane intersecting said axis at an angle other than 90°; and said optical sensing device is positioned along said roll generally at said intermediate position such that said sensing device alternately views portions of the front web surface backed by each of said optical standards as said backing roll rotates.

6. An on-line system in accordance with claim 5, which further comprises an angular position encoder connected to said backing roll for synchronizing system timing to the angular position of said backing roll such that the particular optical standard backing the viewed portion of the front web surface at a given instant in time can be determined.

7. An on-line system in accordance with claim 5, wherein said plane intersects said axis at an angle lower than or equal to 45°.

8. An on-line system in accordance with claim 3, wherein:

said backing roll has an axis of rotation and at least a portion of said surface along the axis is circumferentially divided into at least two portions respectively comprising said two different optical standards; and said optical sensing device is positioned along said roll generally over said circumferentially divided portion such that said sensing device alternately views portions of the front web surface backed by each of said optical standards as said backing roll rotates.

9. An on-line system in accordance with claim 8, which further comprises an angular position encoder connected to said backing roll for synchronizing system timing to the angular position of said backing roll such that the particular optical standard backing the viewed portion of the front web surface at a given instant in time can be determined.

10. An on-line system in accordance with claim 8, wherein:
said circumferentially divided axial portion of said backing roll comprises substantially the entire width of said roll; and
said optical sensing device includes a scanning mounting operable to traverse in a direction parallel to said roll axis such that measurements can be made across the width of the web.

11. An on-line system in accordance with claim 10, which further comprises an angular position encoder connected to said backing roll for synchronizing system timing to the angular position of said backing roll such that the particular optical standard backing the viewed portion of the front web surface at a given instant in time ca be determined.

12. An on-line system in accordance with claim 8, wherein said circumferentially divided portion is circumferentially divided into a plurality of alternating optical standard segments alternately corresponding to said two different optical standards.

13. An on-line system in accordance with claim 12, which further comprises an angular position encoder connected to said backing roll for synchronizing system timing to the angular position of said backing roll such that the particular optical standard backing the viewed portion of the front web surface at a given instant in time ca be determined.

14. An on-line system in accordance with claim 3, wherein:
said backing roll has an axis of rotation and said surface is generally axially divided into two portions respectively comprising said two different optical standards and meeting at a boundary on an intermediate portion on said surface; and
said optical sensing device includes a movable mounting operable to alternately position said optical sensing device over said optical standard portions such that said sensing device alternately views portions of the front web surface backed by each of said optical standards as said sensing device is alternately positioned.

15. An on-line system in accordance with claim 3, wherein:
said backing roll has an axis of rotation and said surface is generally axially divided into two portions respectively comprising said two different optical standards and meeting at a boundary on an intermediate portion on said surface; and
said optical sensing device includes an optical path shifting device to alternately view portions of the front web surface backed by said two optical standard portions.

16. An on-line system in accordance with claim 3, wherein:
said backing roll has an axis of rotation and said surface is axially divided into a plurality of alternating optical standard segments alternately corresponding to said two different optical standards; and
said optical sensing device includes a scanning mounting operable to traverse in a direction parallel to said roll axis such that said optical sensing device alternately views portions of the front web surface backed by segments corresponding to said two different optical standards.

17. An on-line system in accordance with claim 4, wherein:
said backing roll has an axis of rotation and said surface is generally axially divided into two portions respectively comprising said two different optical standards and meeting at a boundary on an intermediate portion on said surface; and
said optical sensing device includes two sets of elements respectively positioned for viewing portions of the front web surface backed by said two different optical standards.

18. An on-line system in accordance with claim 1, wherein at least one optical standard on the surface of said backing roll has a diffuse reflectance spectrum which is essentially the same as the desired reflectivity spectrum of said web.

19. An on-line system in accordance with claim 1, wherein:
said backing roll comprises an optical standard; and
said optical sensing device is arranged to alternately view portions of the front web surface backed by said optical standard and at another location where said web is backed by an air gap.

20. An on-line system in accordance with claim 19, which further comprises at said another location a dark-colored surface backing said web and separated from said web by said air gap.

21. An on-line system in accordance with claim 1, wherein said backing roll has a length less than the width of said web.

22. An on-line system in accordance with claim 1, wherein said optical sensing device comprises an abridged spectrophotometer including an array of detectors for simultaneously measuring reflectance at a plurality of wavelengths.

23. An on-line system in accordance with claim 2, wherein said optical sensing device comprises an abridged spectrophotometer including an array of detectors for simultaneously measuring reflectance at a plurality of wavelengths 24. An on-line system in accordance with claim 3, wherein said optical sensing device comprises an abridged spectrophotometer including an array of detectors for simultaneously measuring reflectance at a plurality of wavelengths.

* * * * *